United States Patent [19]

Menachemoff et al.

[11] 4,402,945
[45] * Sep. 6, 1983

[54] GLYCOSIDE DERIVATIVES OF 6-ETHOXY-1,2-DIHYDRO-2,2,4-TRIMETHYLQUINOLINE AND PHARMACEUTICAL COMPOSITIONS CONTAINING SAME

[75] Inventors: Emil Menachemoff, Tel-Aviv; Oded Awerbuch; Raphael R. G. Haber, both of Givatayim, all of Israel

[73] Assignee: Abic Ltd., Israel

[*] Notice: The portion of the term of this patent subsequent to Dec. 15, 1998, has been disclaimed.

[21] Appl. No.: 261,243

[22] Filed: May 6, 1981

Related U.S. Application Data

[63] Continuation-in-part of Ser. No. 871,455, Jan. 23, 1978, Pat. No. 4,305,932.

[30] Foreign Application Priority Data

Jan. 27, 1977 [IL] Israel .................................. 51342

[51] Int. Cl.$^3$ ...................... A61K 31/70; C07H 19/04
[52] U.S. Cl. .................................... 424/180; 536/23; 536/113
[58] Field of Search .................. 536/23, 113; 424/180; 546/177, 178

[56] References Cited

U.S. PATENT DOCUMENTS 4,305,932 12/1981 Menachemoff et al. ............. 536/23

Primary Examiner—Johnnie R. Brown
Attorney, Agent, or Firm—Steinberg & Raskin

[57] ABSTRACT

The invention provides new glycoside derivatives of 6-ethoxy-1,2-dihydro-2,2,4-trimethylquinoline, to the production thereof and to their use as biological antioxidants, to protect vitamin E-deficient animals and as growth promoting agents.

4 Claims, No Drawings

GLYCOSIDE DERIVATIVES OF 6-ETHOXY-1,2-DIHYDRO-2,2,4-TRIMETHYL-QUINOLINE AND PHARMACEUTICAL COMPOSITIONS CONTAINING SAME

CROSS REFERENCE TO RELATED APPLICATION

This is a continuation in part of our copending application Ser. No. 871,455, filed Jan. 23, 1978, entitled "Ethoxyquin Derivatives, now U.S. Pat. No. 4,305,932".

BACKGROUND OF THE INVENTION

It is known that the compound 6-ethoxy-1,2-dihydro-2,2,4-trimethylquinoline (hereinafter for convenience being referred to as "Ethoxyquin") is an antioxidant and that it acts much like vitamin E in many biological functions. It is further known to protect vitamin E-deficient mice and piglets against iron toxicity (Nature, 846 (1964); Acta Agriculture Scandinavica Suppl. 19 (1973)) and in some cases is more efficient than vitamin E itself. Ethoxyquin is also known to act as a growth promoting agent when added to poultry feed (Quarterly Journal Fla. Acad. Sci. 27 (2), 131 (1964)).

However, Ethoxyquin has certain drawbacks in that it is difficult to produce and to store in pure form. The compound is an oil which rapidly and continuously darkens upon storage. Still further, the compound has an unpleasant taste, it is a base, and administration thereof causes problems.

Research has therefore been conducted to find compounds having the properties of Ethoxyquin without having its disadvantages, namely being antioxidant under biological conditions, being able to protect vitamin E deficient animals, for example from iron poisoning, to act as a growth promoting agent and to inhibit amyloidosis. The compounds desired should also not have the undesirable odor or taste of Ethoxyquin, should be able to be produced in pure suitable form for pharmaceutical compounding and to be storable.

SUMMARY OF THE INVENTION

It is accordingly a primary object of the present invention to provide for the production of compounds having the desired properties of Ethoxyquin without having its undesirable properties.

It is another object of the present invention to provide for the production of such compounds.

It is yet a further object of the present invention to provide growth promoting compositions, compositions for the treatment of vitamin E deficiency and for methods of treating conditions with these compositions.

Other objects and advantages of the present invention will be apparent from a further reading of the specification and of the appended claims.

With the above and other objects in view, the present invention mainly comprises a compound of the formula:

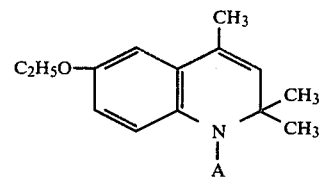

wherein A is

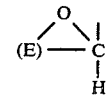

wherein E stands for

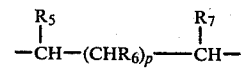

wherein $R_5$, $R_6$ and $R_7$ stands for OH, $CH_2OH$, O-lower carboxyacyl, $CH_2O$-lower carboxyacyl, NHAcyl, COOH, COO-lower alkyl, $CONH_2$, CONH (lower alkyl) and CON (lower alkyl)$_2$ and wherein p=1 or 2.

The compounds of the above formula may be prepared by a process consisting in the reaction of Ethoxyquin with a glycosyl halide bearing protected hydroxyl groups and protected amino groups, if any, in the presence of an acid acceptor. The process may be carried out with or without a solvent, but is prefereably carried out in an inert organic solvent such as benzene, ether acetone, methyl ethyl ketone or dioxane. The reaction may be carried out at ambient or at elevated temperature, e.g., at the boiling point of the solvent.

Organic basis such as triethylamine, N,N-dimethylaniline or event ethoxyquin in excess, or an inorganic base, such as potassium carbonate, may be utilized as the acid acceptor.

As hydroxyl or amino-protecting group there may be utilized, for example, alkyl, aralkyl, or acyl groups, such as methyl, benzyl, acetyl or benzoyl groups. These groups may be split off by per se known methods.

It has been found that compounds of the above formula can be obtained in crystalline or amorphous form, can be easily purified and obtained in a high degree of purity. The compounds are colourless and tasteless. They are stalbe and do not darken during storage. They are soluble to different extents in many organic solvents, e.g., chloroform, dioxane, methanol, ethanol, isopropanol, benzene, either, propylenoglycol, polyethylene glycol, dimethylformamide, N,N-dimethyl-acetamide, isopropylideneglycerol and glycerolformal. Some of the compounds are also soluble to a certain extent in water.

Some of the compounds of the invention undergo slow hydrolysis when dissolved in water forming an extremely fine and stable emulsion in which the ethoxyquin droplets formed are of micron size.

It has been proved that when certain of the compounds of the invention are administered to Vitamin E-deficient mice, the mice are protected from iron poisoning caused by a concurrent administration of an iron preparation. In other words, the Vitamin E-deficient mice are protected against iron poisoning and the biological efficacy of the compounds is thus demonstrated.

The compounds of the invention may be administered either separately or simultaneously with an iron preparation, e.g. iron dextran, or in the form of a mixture therewith. This is very important, since in modern husbandry, iron preparations are administered to new born animals to prevent anaemia and the animals may suffer from Vitamin E-deficiency.

The compounds may be administered in many ways. Thus, they may be admixed to the feed. Another form of administration of the compounds which are water soluble or suspendable is as part of drinking water. In some cases the compounds may be administered also in the form of an injection.

The present invention thus also comprises pharmaceutical preparations (human and veterinary) containing as active compound a compound of the invention.

The present invention further comprises a feed additive or additive to the drinking water of animals containing a compound of the invention.

DESCRIPTION OF PREFERRED EMBODIMENTS

The present invention will be further illustrated by the following examples. The scope of the invention is not, however, meant to be limited to the specific details of the examples. In all examples the temperatures are in degrees centigrade, and all melting points are uncorrected.

EXAMPLE 1

Ethoxyquin (240 g) and 2,3,4,6-tetra-O-acetyl-α-D-glucopyranosyl bromide (228 g) were stirred at 80° for 18 hours. Acetone (200 ml) was added to the hot reaction mixture and stirring continued for an additional 20 minutes. After cooling, the solid ethoxyquin hydrobromide was filtered off, washed thoroughly with acetone and the combined acetone filtrates were evaporated under reduced pressure. The resulted crude product was recrystallised (iso-propanol) to yield 226.5 g of 1-(2,3,4,6-tetra-O-acetyl-D-glucopyranosyl)-6-ethoxy-1,2-dihydro-2,2,4-trimethylquinoline. m.p.: 180°–181°.

$\nu_{max}^{KBr}$: 3.30; 5.65; 6.15; 6.30; 6.65; 6.70; 6.90; 7.00; 7.20; 7.30; 7.40; 7.65; 7.75; 8.00; 8.35; 8.50; 8.60; 9.10. 9.00; 9.35; 9.60; 10.10; 10.40; 10.45; 10.90; 11.25; 11.65; 11.95; 12.15; 12.90; 13.30; 13.70; 14.85μ.

$\delta$CDCl$_3$: 1.10 s(3H); 1.38 t(J=7.0 Hz; 3H); 1.43 s(3H); 1.78 s(3H); 1.85 s(6H); 2.03 s(3H); 2.08 s(3H); 3.55–4.33 m, 4.70–5.55 m(10H); 6.55–6.80 m(2H); 7.15–7.40 m(1H) ppm.

The compound was colourless, odourless and tasteless.

EXAMPLE 2

1-(2,3,4,6-tetra-O-acetyl-D-glucopyranosyl)-6-ethoxy-1,2-dihydro-2,2,4-trimethylquinoline (35 g) was suspended in absolute CH$_3$OH (350 ml). NaOCH$_3$(2,2 M, 2 ml) was added to the stirred reaction mixture. Dissolution of the solid was completed after 110 minutes. The solution was neutralized by acidic resin (Amerlite IR-120 (H+), then filtered, and the filtrate was evaporated under reduced pressure, leaving a white, amorphous solid being 24.2 g of 1-D-glucopyranosyl-6-ethoxy-1,2-dihydro-2,2,4-trimethylquinoline (hereinafter called "ethoxyquin-glucoside"). The compound was odourless.

$\nu_{max}^{KBr}$: 2.45; 3.40; 6.20; 6.35; 6.70; 7.20; 7.70; 7.90; 8.25; 8.50; 9.25; 9.50; 9.90; 10.30; 10.70; 11.15; 11.45; 12.30; 13.00; 13.40; 13.70μ.

$\delta$CDCl$_3$: 1.00–1.50 m (9H); 1.93 m (3H); 2.80–5.10 m (13H); 5.45 m (1H); 6.45–6.80 m (2H); 7.0–7.35 m (1H) ppm.

EXAMPLE 3

Ethoxyquin (230 g) and 2,3,4,6-tetra-O-acetyl-αD-galactopyranosyl bromide (218 g) were stirred together at 80° for 17 hours. Acetone (400 ml) was added to the hot reaction mixture and stirring was continued for an additional 20 minutes.

After cooling the precipitated ethoxyquin-hydrobromide was filtered off, washed with acetone and the filtrate was evaporated to dryness under reduced pressure.

The crude product was recrystallised (isopropanol) yielding 123.0 g of a white, crystalline product being 1-(2,3,4,6-tetra-O-acetyl-D-galactopyranosyl)-6-ethoxy-1,2-dihydro-2,2,4-trimethylquinoline. m.p. 150°–151°.

$\nu_{max}^{KBr}$: 3.40; 5.70; 6.05; 6.20; 6.35; 6.70; 7.00; 7.30; 7.70; 8.20; 9.00; 9.20; 9.50; 9.85; 10.40; 10.55; 10.90; 11.40; 12.15; 12.40; 13.00; 13.55; 13.70; 14.00; 14.95μ.

$\delta$CDCl$_3$: 1.10 s(3H); 1.37 t(J=7 Hz; 3H); 1.41 s(3H); 1.85 s(3H); 1.98 s(6H); 2.14 s(3H); 2.23 s(3H); 3.75–4.40 m, 4.65–6.00 m(10H); 6.55–6.83 m(2H); 7.30–7.65 m(1H) ppm.

EXAMPLE 4

NaOCH$_3$(2,2 M, 0.5 ml) was added at room temperature to a stirred solution of 1-(2,3,4,6-tetra-O-acetyl-D-galactopyranosyl)-6-ethoxy-1,2-dihydro-2,2,4-trimethylquinoline (50 g) in abs. MeOH (50 ml). After 1 hour the solution was neutralized (glacial HOAc). The solution was filtered and the filtrate was evaporated to dryness under reduced pressure. The crystalline product was recrystallized from ethanol, yielding 2.9 g of 1-D-glactopyranosyl-6-ethoxy-1,2-dihydro-2,2,4-trimethylquinoline (hereinafter called "ethoxyquin-galactoside"). mp: 162°–163°.

$\nu_{max}^{KBr}$: 3.00; 3.40; 6.35; 6.70; 7.00; 7.10; 7.20; 7.35; 7.45; 7.60; 7.70; 8.00; 8.35; 8.80; 9.15; 9.30; 9.60; 10.15; 10.60; 10.90; 11.20; 11.55; 11.80; 12.10; 12.75; 13.35; 14.10μ.

$\delta$D$_6$-DMSO: 0.8–1.65 m(9H); 1.83 m(3H); 3.00–5.00 m(13H); 5.40 m(1H); 6.30–6.70 m(2H); 7.28–7.65 m(1H) ppm.

EXAMPLE 5

2-Acetamido-3,4,6-tri-O-acetyl-D-glucopyranosyl chloride (18.3 g) and ethoxyquin (22.1 g) were vigourously stirred together at 80° for 3 hours. Acetone (50 ml) was added to the hot reaction mixture and stirring was continued for 0.5 hours. After cooling, the solid ethoxyquin-hydrochloride was filtered, washed with acetone and the combined filtrates were evaporated under reduced pressure. The crude product was purified by column chromatography on silica (ethylacetate-benzene 1:4). 16.5 g of 1-(2-acetamido-3,4,6-tri-O-acetyl-2-deoxy-D-glucopyranosyl)-6-ethoxy-1,2-dihydro-2,2,4-trimethylquinoline were obtained. Analytical grade sample was obtained by recrystallisation from ether or isopropanol. m.p. 186°–187°.

$\nu_{max}^{KBr}$: 3.00; 3.20; 3.30; 5.65; 5.95; 6,30; 6.65; 6.95; 7.25; 7.65; 8.05; 8.65; 8.85; 9.10; 9.55; 10.00; 10.50; 10.80; 11.25; 11.70; 11.90; 12.25; 12.80; 13.30; 13.65; 14.90μ.

$\delta$CDCl$_3$: 1.08 s(3H); 1.25–1.55 m(6H); 1.55 s(3H); 1.85–2.18 m(12H); 3.65–4.38 m(6H); 4.88–5.92 m(5H); 6.60–6.85 m(2H); 7.15–7.45 m(1H) ppm.

EXAMPLE 6

To a solution of 1-(2-acetamide-3,4,6-tri-O-acetyl-D-glucapyranosyl)-6-ethoxy-1,2-dihydro-2,2,4-trimethylquinoline (5.0 g) in abs.CH$_3$OH (150 ml), NaOCH$_3$ (2.2 M, 0.5 ml) was added. The solution was stirred at room temperature for 2 hours and then neutralized with Amerlite-IR-120 (H$^+$).

The resin was filtered off and the filtrate was evaporated to dryness under reduced pressure, yielding 3.85 g of a white, amorphous solid being 1-(2-acetamido-2-deoxy-D-glucopyranosyl)-6-ethoxy-1,2-dihydro-2,2,4-trimethylquinoline. Recrystallisation from ethanol-ether or ethanol-ethylacetate. m.p.: 114.5°–116°.

$\nu_{max}^{KBr}$: 3.00; 3.40; 6.05; 6.40; 6.70; 6.95; 7.25; 7.70; 7.95; 8.30; 8.45; 8.55; 8.70; 9.00; 9.30; 9.55; 10.00; 10.45; 10.70; 11.20; 11.55; 11.75; 12.35; 13.00; 13.45; 13.80$\mu$.

$\delta$CDCl$_3$: 0.90–2.15 m(15H); 3.15–0.25 m(9H); 4.60–4.95 m(1H); (+D$_2$O) 5.45 m(1H); 6.68 m(2H); 7.25 m(1H) ppm.

EXAMPLE 7

2,3,4-Tri-O-acetyl-α-D-xylopyranosyl bromide (18.8 g) and ethoxyquin (29.2 g) were stirred together at 70° for 6 hours. Acetone (100 ml) was added to the hot solution and stirring continued for 15 minutes. After cooling, the ethoxyquinhydrobromide was filtered off, washed with acetone and the combined filtrates were evaporated to dryness under reduced pressure yielding brown syrup (35.3 g). Part of the crude reaction product (12.5 g) was purified by column chromatography on silica (ethylacetate-benzene) (1:9) and 5.9 g of 1-(2,3,4-tri-O-acetyl-D-xylopyranosyl)-6-ethoxy-1,2-dihydro-2,2,4-trimethylquinoline, was obtained as a highly viscous syrup, which crystallised from isopropanol. m.p. 71°–72°.

$\nu_{max}^{KBr}$: 3.35; 3.65; 6.15; 6.30; 6.65; 6.95; 7.30; 7.50; 8.15; 8.65; 8.95; 9.50; 10.15; 10.40; 10.65; 10.95; 11.40; 11.65; 11.95; 12.10; 12.25; 12.70; 12.90; 13.35; 13.70; 13.95; 14.50; 14.90$\mu$.

$\delta$CDCl$_3$: 1.10 s(3H); 1.37 t(J=7.0H); 1.42 s(6H); 1.78 s(3H); 1.95 s(6H); 2.03 s(3H); 3.15–3.55 m(1H); 3.75–4.35 m(3H); 4.60–5.60 l m(5H); 6.58–6.68 M(2H); 7.20–7.50 m(1H) ppm.

EXAMPLE 8

To a solution of 1-(2,3,4-tri-6-acetyl-D-xylopyranosyl)-6-ethoxy-1,2-dihydro-2,2,4-trimethyl-quinoline (3.2 g) in abs. CH$_3$OH ((25 ml), NaOCH$_3$ (2.2 M, 0.3 ml) was added. The reaction mixture was stirred at room temperature for 10 minutes, then neutralised (Amberlite IR-120 H$^+$), filtered and the filtrate was evaporated to dryness under reduced pressure, yielding 1.0 g of 1-D-zylopyranosyl-6-ethoxy-1,2-dihydro-2,2,4-trimethylquinoline as white amorphous solid.

$\nu_{max}^{KBr}$: 2.95; 3.40; 6.20; 6.35; 6.70; 6.95; 7.20; 7.35; 7.60; 7.90; 8.25; 8.45; 8.50; 8.70; 8.95; 9.15; 9.50; 10.15; 10.50; 11.10; 11.45; 11.65; 12.30; 12.95; 13.35; 13.70; 14.90$\mu$.

$\delta$CDCl$_3$: 0.95–1.53 m(9H); 1.95 m(3H); 2.80–4.60 m(11H); 5.45 m(1H); 6.50–6.80 m(2H): 7.10–7.38 (1H) ppm.

EXAMPLE 9

A mixture of methyl (tri-O-acetyl-D-glucopyranosyl-bromide)-uronate (4.9 g) and ethoxyquin (5.4 g) was heated to 80° and stirred together for 12 hours. Acetone (40 ml) was added and the ethoxyquin-hydrobromide obtained was filtered off. The filtrate was evaporated to dryness under reduced pressure. The crude product was purified on a silica column, (benzene-ethylacetate 18:1) to yield 4.0 g of 1-(methyl tri-O-acetyl-D-glucopyranosylurono)-6-ethoxy-1,2dihydro-2,2,4-trimethylquinoline; m.p.: 122.5°–123° (methanol).

$\nu_{max}^{KBr}$: 3.35; 5.65; 6.15; 6.30; 6.65; 6.75; 6.95; 7.00; 7.20; 7.45; 8.05; 8.15; 8.80; 9.05; 9.40; 9.55; 9.65; 9.80; 10.20; 10.75; 11.05; 11.25; 11.45; 11.65; 12.40; 12.70; 13.50; 13.70; 14.70; 14.95$\mu$.

$\delta$CDCl$_3$: 1.10 s(3H); 1.38 t(J=7.0H); 1.41 s(6H); 1.78 s(3H); 1.85–2.13 m(9H); 3.75 s(3H); 3.80–4.23 m, 4.68–5.53 m(8H); 6.60–6.85 m(2H); 7.20–7.48 (1H) ppm.

EXAMPLE 10

2.2 M NaOCH$_3$ (0.4 ml) was added to a solution of 1-(methyl-tri-O-acetyl-D-glucopyranosylurono)-6-ethoxy-1,2-dihydro-2,2,4-trimethylquinoline (1.0 g) in abs. methanol (50 ml). The solution obtained was stirred for 1 hour at room temperature, then neutralized with Amberlite IR-120(H$^+$). The resin was filtered off, the filtrate was treated with active charcoal, filtered and evaporated under reduced pressure, yielding 1-(methyl-D-glucopyranosylurono)-6-ethoxy-1,2-dihydro-2,2,4-trimethylquinoline as colourless, amorphous solid (0.62 g).

$\nu_{max}^{KBr}$: 2.90; 3.10; 3.35; 5.70; 6.20; 6.35; 6.75; 6.85; 6.95; 7.20; 7.35; 7.45; 7.75; 7.90; 8.05; 8.30; 8.40; 8.70; 9.10; 9.20; 9.55; 9.80; 9.95; 10.10; 10.30; 10.70; 11.10; 11.50; 11.60; 12.30; 12.80; 13.45; 13.75; 14.20; 16.0$\mu$.

$\delta$D$_6$DMSO: 1.00–1.55 m(9H); 1.95 m(3H); 3.75 m: 3.10–4.25 m, 4.40–4.75 m; 4.90–5.43 m(13H); 5.50 m(1H); 6.48–6.85 m(2H); 7.13–7.45 m(1H) ppm.

EXAMPLE 11

1-(Methyl tri-O-acetyl-D-glucopyranosylurono)-6-ethoxy-1,2-dihydro-2,2-4-trimethylquinoline (0.5 g) was dissolved in abs. methanol (50 ml) saturated with ammonia. The solution obtained was kept for 18 hours at 8°. Then it was evaporated to dryness under reduced pressure. The residue was dissolved in methanol and the solution obtained was treated with active charcoal, filtered and evaporated to dryness to yield 1-(D-glucopyranoxyluronamide)-6-ethoxy-1,2-dihydro-2,2,4-trimethylquinoline as colourless solid. m.p.: 114°–115°.

$\gamma_{max}^{KBr}$: 2.90–3.05; 3.35; 3.40; 3.50; 5.95; 6.20; 6.35; 6.75; 7.00; 7.05; 7.20; 7.35; 7.80; 8.25; 8.55; 8.70; 9.00; 9.20; 9.50; 9.85; 10.30; 11.00; 11.50; 11.60; 12.30; 13.00; 13.45$\mu$.

$\rho$CDCl$_3$: 1.05–1.53 m(9H); 1.95 m(3H); 2.75–5.00 m(12H); 5.55 m(1H); 6.32–6.75 m(2H); 7.05–7.35 m(1H) ppm.

EXAMPLE 12

Ethoxyquin glucoside (5 g) is dissolved in propylene glycol (95 g) by mixing under sterile conditions, to yield a solution which can be used for injections.

EXAMPLE 13

A mixture comprising:
Ethoxyquin galactoside: 5.0 g
Lactose: 15.0 g
Soyabean meal: 80.0 g
is admixed thoroughly in a Fisher-Kendall mixer to yield a mixture which can be utilized as a premix for animal feedstuffs.

EXAMPLE 14

Ethoxyquin galactoside (50 parts) and Lactose U.S.P. grade (200 parts) are granulated together with a 10% solution of Polyvinylpyrrolidone (PVP)-K30 in isopropanol. To the dried and sifted granulate, 5% of dry starch and 0.3% of Magnesium Stearate are added and well mixed. The whole mass is compressed to tablets each weighing about 0.265 g and each containing 50 mg of ethoxyquin galactoside.

In the following Examples the activity of some of the compounds of general formula I is illustrated. Albino mice were used in all examples. The mice of group A received a low Vitamin E concentration diet (8 ppm) for 6 weeks starting 12 days after birth. This treatment caused a remarkable Vitamin E deficiency and a considerably increased sensitivity to iron poisoning. Group B mice received the regular commercial food (Vit. E. conc. 150 ppm). Both groups of mice were of the same age.

EXAMPLE 15

Fifteen Vitamen E deficient mice (Vitamin E blood level 0.2 mg %) of group A and 20 regularly fed mice (Vitamin E blood level 1.4 mg %) of group B were injected i.p. with a 10% solution of an Iron Dextran complex at a level of 1000 mg Fe/Kg body weight. The mortality observed after 5 days in group A was 14/15 and in group B 1/20.

EXAMPLE 16

Eight Vitamin E-deficient mice were injected s.c. with a 20% solution of ethoxyquin-glucoside in propyleneglycol at a level of 200 mg/kg body weight. A 10% solution of the Iron-Dextran complex was immediately injected i.p. at a level of 1000 mg/kg body weight. The mortality observed after 5 days was ⅛.

EXAMPLE 17

Example 16 was repeated exactly but the ethoxyquin-glucoside solution was injected s.c., at a level of 400 mg/kg body weight, on 10 mice. The mortality observed after 5 days was 0/10.

EXAMPLE 18

A mixture of a 10% iron-dextran solution and 20% solution of the ethoxyquin-glucoside in propyleneglycol was prepared and injected i.p. to 8 Vitamin E-deficient mice at a level of 1000 mg of Fe and 200 mg of glucoside/Kg body weight. The mortality observed after 5 days was ⅛.

EXAMPLE 19

Example 16 was repeated, but ethoxyquin-galactoside was used instead of ethoxyquin-glucoside. The mortality observed after 5 days was 2/8.

EXAMPLE 20

Example 16 was repeated on nine mice, but 1-(2-acetamide-3,4,6-tri-O-acetyl-D-glucopyranosyl)-6-ethoxy-1,2-dihydro-2,2,4-trimethylquinoline in dimethyl sulfoxide (DMSO) was used in a level of 250 mg/kg body weight instead of ethoxyquin-glucoside in propylene glycol. The mortality observed after 5 days was 2/9.

EXAMPLE 21

Example 18 was repeated, but 1-(2-acetamido-D-glucopyranosyl)-6-ethoxy-1,2-dihydro-2,2,4-trimethylquinoline was used instead of ethoxyquin-glucoside. The mortality observed after 5 days was ⅛.

EXAMPLE 22

Example 18 was repeated on 10 mice, but 1-C-xylopyranosyl-6-ethoxy-1,2-dihydro-2,2,4-trimethylquinoline was used instead of ethoxyquin-glucoside. The mortality observed after 5 days was 1/10.

EXAMPLE 23

A finely powdered dry mixture of iron-dextran powder (3.3 g) containing 30% of Fe, ethoxyquin-glucoside (0.2 g) and NaCl (0.1 g) was dissolved with good shaking in water for injection, to yield 10 ml of solution. The solution prepared in this way was injected i.p. to 9 Vitamin E-deficient mice at a level of 100 mg of Fe and 200 mg of ethoxyquin-glucoside/kg body weight. The mortality observed after 5 days was 0/9.

EXAMPLE 24

Eight Vitamin E deficient mice received a daily s.c. injection of ethoxyquin gluconamide pentacetate for three consecutive days. The doese per injection were equivalent to 100 mg of ethoxyquin/Kg animal weight. The compound tested was dissolved in propylene glycol, so as to provide the required dose by injecting 0.1 ml of the solution per 10 g body weight. Iron Dextran solution (1000 mg Fe/Kg body weight) was injected i.p. together with the last injection of ethoxyquin gluconamide pentacetate. The observed mortality after 5 days was ⅛.

EXAMPLE 25

Finely ground Vitamin E deficient food was homogenously mixed with ethoxyquin galactoside and adjusted to a concentration of 0.2% w/w ethoxyquin equivalent.

Two groups (A and B) of eight Vitamin E deficient mice were fed at libitum with the above food. After 3 days of feeding the animals of Group A received an i.p. Iron Dextran injection (1000 mg Fe/Kg body weight).

Group B received the same i.p. injection but after seven days feeding.

The animals were observed during 5 consecutive days following the Iron Dextran injections.

The observed mortality was: 2/8 for Group A (three day feeding); 0/8 for Group B (seven day feeding).

While the invention has been illustrated with respect to the production and use of specific compounds, it is found that variations and modifications of the invention can be made.

What is claimed is:

1. A compound of the formula:

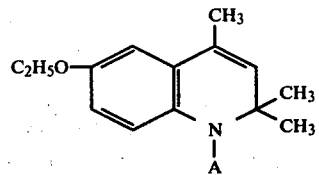

wherein A is

wherein E stands for

wherein $R_5$, $R_6$ and $R_7$ stands for OH, $CH_2OH$, O-lower carboxyacyl, $CH_2O$-lower carboxyacyl, NH-lower carboxyacyl, COOH, COO-lower alkyl, $COHN_2$, CONH (lower alkyl) and CON (lower alkyl)$_2$, and wherein p=1 or 2.

2. A pharmaceutical composition for use in the treatment of Vitamin E-deficient animals, comprising an inert carrier, a Vitamin E deficiency treatment effective amount of the compound of claim 1 and iron dextran.

3. Animal feed composition for use in treatment of Vitamin E-deficient animals, comprising an animal food stuff and a Vitamin E deficiency treatment effective amount of the compound of claim 1.

4. Liquid composition for use in treatment of Vitamin E-deficient animals, comprising drinking water and a Vitamin E deficiency treatment effective amount of the compound of claim 1.

* * * * *